United States Patent [19]

Kushner et al.

[11] Patent Number: 4,954,236
[45] Date of Patent: Sep. 4, 1990

[54] APPARATUS AND METHOD FOR GEL CASTING AND ELECTROPHORESIS IN A SINGLE ENCLOSURE

[75] Inventors: Gregory Kushner, Richmond; Timothy E. Delony, Hercules, both of Calif.

[73] Assignee: Bio-Rad Laboratories, Inc., Hercules, Calif.

[21] Appl. No.: 373,118

[22] Filed: Jun. 28, 1989

[51] Int. Cl.[5] ................... G01N 27/28; G01N 27/26; B61D 57/02
[52] U.S. Cl. ........................ 204/299 R; 204/182.8; 249/161
[58] Field of Search ............ 204/299 R, 182.8, 182.9, 204/187.7, 180.1; 264/316, 313, 219, 216, 2.2; 249/82, 117, 121, 161

[56] References Cited

U.S. PATENT DOCUMENTS

| | | | |
|---|---|---|---|
| 3,879,280 | 4/1975 | Peterson et al. | 204/182.8 X |
| 4,560,459 | 12/1985 | Hoefer | 204/299 R X |
| 4,795,541 | 1/1989 | Hurd et al. | 204/182.8 X |

OTHER PUBLICATIONS

Isolab, Inc. Literature on Electrophoresis Products.
Schleicher & Schuell Literature on S&S Profile Polyacrylamide Gels.
Jule, Inc. literature on Precast Gels.

*Primary Examiner*—John F. Niebling
*Assistant Examiner*—John S. Starsiak, Jr.
*Attorney, Agent, or Firm*—Townsend and Townsend

[57] ABSTRACT

Slab gels are cast in a gel enclosure which consists of a flat rectangular plate held against a larger plate by a flexible sealing sheet with a removable edge. The smaller plate is retained within raised edges along three sides of the larger plate and rests on a pair of shoulders along two of the raised edges. The sealing sheet spans all three raised edges and the smaller plate resting between them, thereby sealing three sides of the chamber between the plates, the width of the chamber being established by the shoulders. One edge of the sealing sheet is removable to expose the lower end of the gel slab to a buffer solution to permit the performance of an electrophoretic separation in the enclosure once the gel has been formed. A depression in the raised edge underlying the removable edge of the sealing sheet increases the access of a buffer solution to the lower end of the gel slab during electrophoresis.

15 Claims, 2 Drawing Sheets

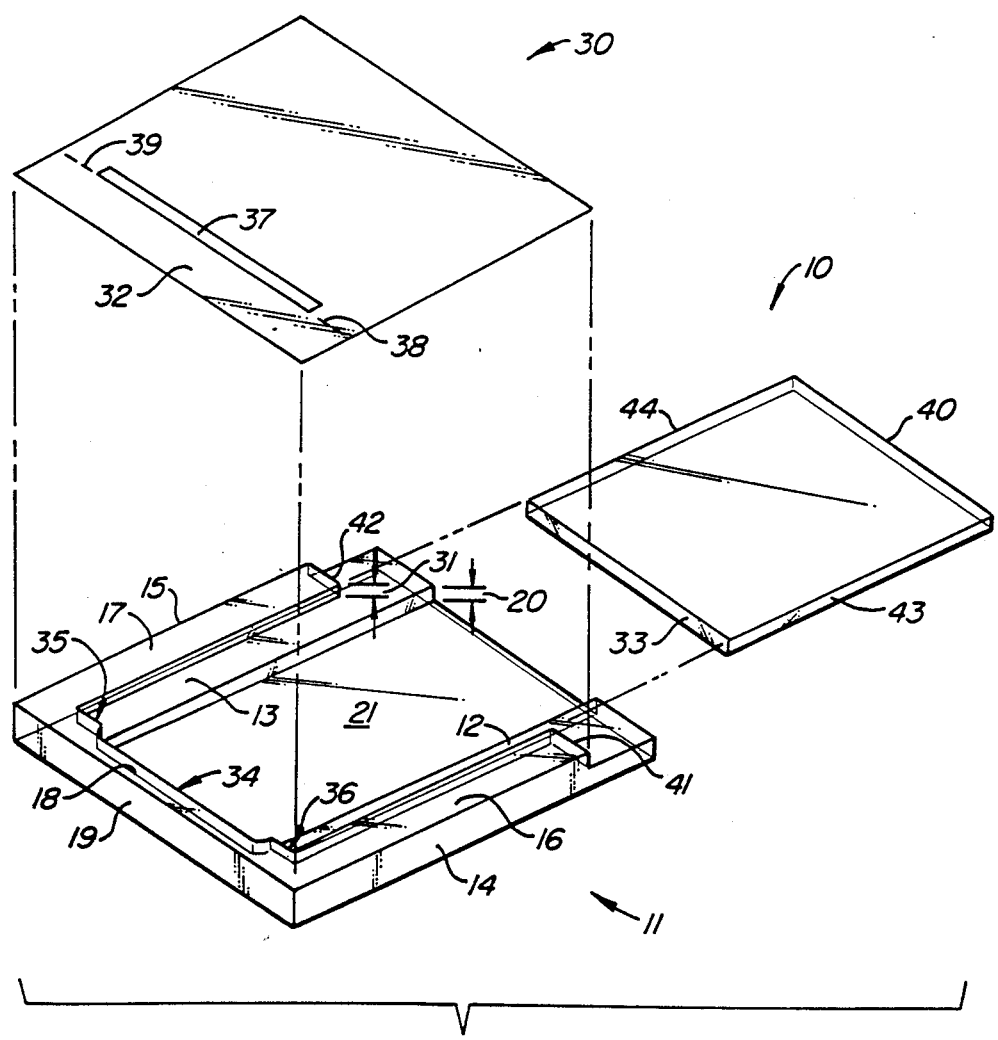
FIG._1.

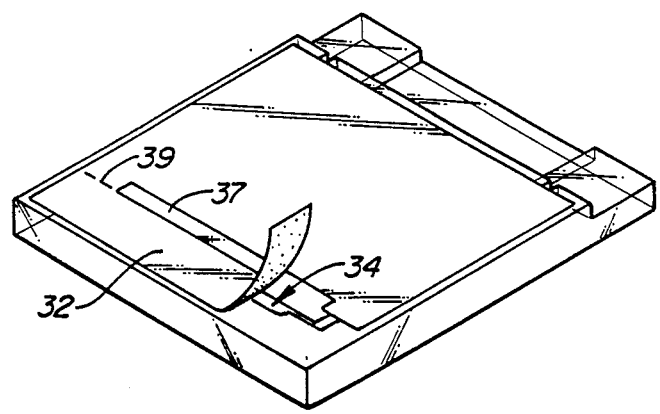
FIG._2.
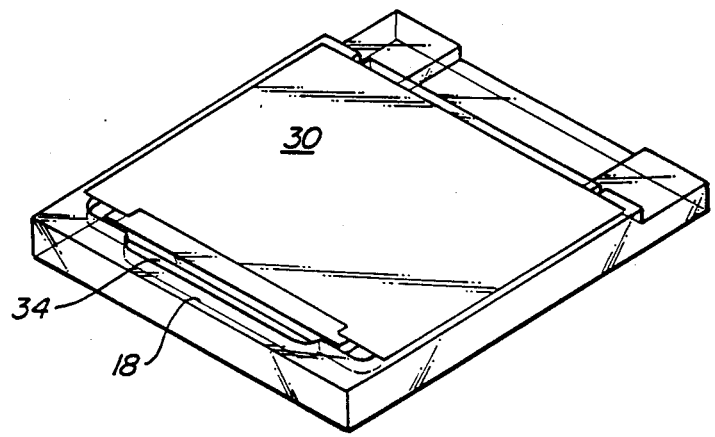
FIG._3.

APPARATUS AND METHOD FOR GEL CASTING AND ELECTROPHORESIS IN A SINGLE ENCLOSURE

This invention relates to electrophoresis in slab gels.

BACKGROUND OF THE INVENTION

The preparation and use of slab-shaped gels for electrophoretic separations generally require delicate handling through a time-consuming sequence of manipulations by the laboratory technician. The gel is first cast in a mold, then transferred to a support or enclosure which allows the passage of electric current for electrophoresis. The mold of course must be leakproof, yet during electrophoresis the gel must have two opposing ends exposed to permit contact with buffer solutions in which the electrodes are placed. The transfer presents many opportunities for error and nonreproducibility, as well as the danger of ruining a gel and the loss of an analysis as well as valuable laboratory time. Subsequent to electrophoresis, the plates of the mold must be capable of being separated to permit staining of the gel, presenting further problems in leakproofing.

These problems are well illustrated by commercial products currently available for slab gel electrophoresis. A typical gel enclosure consists of two flat plates separated by spacers along two opposing longitudinal edges, the transverse edges remaining open, and the plates held together by compression along the longitudinal edges. To cast the gel between the two plates the assembled arrangement consisting of the plates, spacers, and whatever clamps are used to hold the plates and spacers together, are placed on a casting stand where one of the open edges of the plate assembly is pressed against a resilient sealing material such as rubber. The gel solution is then poured between the plates through the remaining open end. Once the gel has solidified, the plate assembly is removed from the casting stand and connected to appropriate components which permit the electrical connections needed for electrophoresis.

This procedure has several disadvantages. First, the plate assembly must be forced against the rubber surface with pressure to eliminate leakage. Second, an effective seal against the rubber surface also requires the plates and spacers to be carefully aligned and tightly compressed against each other. Such forces create a risk of disturbing the delicate gel, either during transfer from the casting stand to the cell which supplies the electrical connection, or during the final disassembly of the plates for removal and analysis of the gel. Third, the casting stand is an additional piece of equipment, raising the cost of the apparatus. Fourth, this multitude of manipulations and components makes the preparation and use of slab gels an expensive and cumbersome procedure, one which is not well suited to mass production or automation.

SUMMARY OF THE INVENTION

Apparatus has now been developed which permits the casting of a slab gel without the use of a casting stand, as well as the passage of an electric current for electrophoresis in the same gel enclosure. This invention thus resides in an assembly which serves as a leakproof mold for a slab gel, with a sealing sheet from which a section may be removed to expose one edge of the slab gel thus formed. The edge thus exposed, together with an exposed edge on the opposing side of the gel, permit contact with buffer solutions and hence an electrophoretic separation.

Sealing is achieved without compression, thereby minimizing any risk of damage to the gel during handling. Further, the lack of need of a casting stand reduces the number of components required, as well as the risk of leakage and the number of manipulative steps involved in carrying out the procedure. Still further, the structure lends itself readily to the production of precast gels in quantity, enhancing reproducibility and reducing cost.

Various aspects of the invention include the gel enclosure, casting and electrophoretic methods involving its use, and precast gels prepared and contained in the enclosure. Other aspects, features and advantages of the invention become apparent from the description which follows.

BRIEF DESCRIPTION OF THE DRAWINGS

FIG. 1 is an exploded perspective view of a gel enclosure in accordance with the present invention.

FIG. 2 is a perspective view of the gel enclosure of FIG. 1 with one end of the sealing sheet being removed.

FIG. 3 shows the gel enclosure of FIG. 2 ready for electrophoresis.

DETAILED DESCRIPTION OF THE INVENTION AND PREFERRED EMBODIMENTS

In the embodiment shown in the drawings, the gel enclosure is constructed of a flat rectangular plate 10 and a second, larger plate 11 equipped with appendages designed to receive the smaller plate 10, serve as a guide for its position, and establish the thickness of the chamber in which the gel is to be formed. These appendages include shoulders 12, 13 along the two longitudinal sides 14, 15, respectively, of the second plate and three raised edges, two of which 16, 17 are along the longitudinal sides, and the third 18 along one of the transverse sides 19. The smaller plate 10 fits between the lateral raised edges 16, 17, and rests on both shoulders 12, 13.

The shoulders in this embodiment of the invention are of equal height 20, the height being constant along their length. The shoulders serve as spacers to establish the gap width between the smaller plate 10 and the flat surface 21 between the shoulders of the larger plate. This gap width will be the width of the slab gel formed between these two plates. Variations may be made in this arrangement to meet the needs of particular electrophoretic systems. For example, the two shoulders may be of unequal height, or may be of either increasing or decreasing height along their length. The appropriate choice for any particular separation will be readily apparent to one skilled in the art, based upon the particular species being separated, the type of separation sought and possibly also the type of gel to be formed in the space.

A third element in the assembly is a fluid-impermeable sealing sheet 30 which spans the raised edges 16, 17, 18 of the second plate, and the space between them. The sealing sheet is preferably of flexible material, and has an adhesive coating on its underside, causing it to adhere to the raised edges 16, 17, 18 and the upper surface of the flat plate 10 resting between them. The sealing sheet thus seals off all spaces between the flat plate 10 and the raised edges of the second plate, preventing liquid leakage along the three sides of the flat plate 10. The rectangular slab-shaped chamber defined by the opposing surfaces of the two plates and the thickness of the shoulders 12, 13 is thus sealed along three sides and open along the fourth. To facilitate the seal, the three raised edges 16, 17, 18 are preferably coplanar. i.e., all at the same height above the flat central surface 21 of the larger plate, and the height 31 of the lateral raised edges 16, 17 above the shoulders 12, 13 is equal to the thickness of the smaller plate 10. With the dimensions thus selected, the two plates when combined form a coplanar surface which includes the raised edges of the larger plate and the upper surface of the smaller plate, facilitating the ability of the sealing sheet 30 to form a leak proof seal.

The sealing sheet 30 is of a material which permits removal of a strip 32 along one transverse edge, which is the edge running along the transverse raised edge 18 of the larger plate. The removable strip 32 is sufficiently wide to entirely cover the end edge of the smaller plate 10 which is adjacent the transverse raised edge 18. Thus, when the removable strip 32 is severed from the remainder of the sealing sheet 30 and removed as shown in FIG. 2, the end edge 33 of the smaller plate is fully exposed. The strip 32 is removed after the gel has been cast and before the assembly is placed in contact with buffer solutions for electrophoresis. Removal of the strip thus permits contact of the edge of the gel underlying the end edge 33 of the smaller plate with a buffer solution.

Contact with the buffer solution along this edge is further facilitated by a depression 34 or concave contoured portion along the inner side of the raised edge 18. This depression 34 occupies only a central portion of the raised edge 18 leaving two flat surface 35, 36, one on either side. Since the end edge 33 of the smaller plate is wider than the depression, the end edge 33 abuts the flat surfaces 35, 36, leaving an opening between the smaller plate 10 and the raised transverse edge 18 defined by the depression 34. This opening is fully covered by the removable strip 32 of the sealing sheet while the gel is being cast. As the gel solution is poured into the open space between the plates, this opening is filled as well. The solidified gel thus extends into the opening, thereby providing ample surface area for contact between the end edge of the gel and a buffer solution in which that end of both plates is immersed.

The sealing sheet may be any material which can be made to adhere to the plates in a fluid-impermeable manner, thereby permitting one to place the assembly in a vertical position, fill the interior volume with a gel solution, and permit the gel to polymerize without experiencing any leakage. Any materials known in the art to serve this purpose may be used as the sealing sheet. A preferred example is a flexible polymeric sheet with an adhesive coating on the side facing the plates. Label stock or other similar materials may be used. Particularly preferred polymers are polyesters. The adhesive coating may be any adhesive known in the art, particularly those which are water insoluble. Examples include silicone and acrylic adhesives, notably Acrylic No. 300, No. 320 and No. 400 of the 3M Company St. Paul, Minn.

The character of removability of the end strip 32 refers to the fact that the strip be severable from the remainder of the sealing sheet and, once severed, removable from the plates without disturbing the remainder of the sealing sheet. Materials in which this can be accomplished by hand in a quick and easy manner by the user are preferred. This includes cutting the sheet with a blade, preferably hand held, tearing the sheet along a perforated line, and other similar means. In the embodiment shown in the drawings, the sealing sheet has a central elongate strip 37 along the inner edge of the strip, defining the line along which the strip is to be severed from the remainder of the sheet. Guide lines 38, 39 are drawn, painted or printed on the sheet, extending the strip to the side edges of the sheet, as a guide to the use for cutting with a knife blade.

Once the strip is severed, it is easily removed as shown in FIG. 2. The final assembly, with gel cast and end strip removed, as shown in FIG. 3, is ready for insertion into an electrophoresis cell for an electrophoretic separation.

The loading of samples onto the gel for electrophoresis may be accomplished using conventional techniques. For instance, a comb-shaped insert may be placed in the open end of the chamber formed between the two plates after the gel solution has been added but before solidification has occurred. Once the gel is cast, the insert is removed, leaving wells corresponding to the teeth of the comb, for placement of liquid samples.

In the embodiment shown in the drawings, it will be noted that the lateral raised edges 16, 17 are truncated at one end, thereby extending less than the full length of the larger plate. The smaller plate is of a length equal to the lengths of these lateral raised edges such that when the smaller plate is inserted between the raised edges, the smaller plate and the lateral raised edges are coterminous, i.e., the exposed edge 40 of the smaller plate is aligned with the truncated ends 41, 42, giving the assembled pieces a stepped profile. This permits the assembly to be inserted into slab-type electrophoresis cells designed for gel enclosures with stepped profiles as a means of contacting the upper and lower gel edges with upper and lower buffer solutions, respectively. One example is the PROTEAN II cell of Bio-Rad Laboratories. Inc.. Hercules, Calif., as disclosed and described in U.S. Pat. No. 4.574.040, which is incorporated herein by reference.

Once electrophoresis is complete, the gel enclosure is removed from the cell, the sealing sheet 30 is cut along the clearance lines between the raised edges 16 and 17 of the larger plate 11 and the lateral edges 43, 44 of the smaller plate 10, and the plates separated. The gel may then be stained if desired, and processed in general according to conventional procedures for reading or analyzing the gels, or for isolating the separate components.

The plates themselves may be formed from any conventional material which is inert and compatible with the gels and the species being separated. Glass and plastic, preferably transparent, are widely used for components of this type. It will be particularly convenient to use clear plastic for the large plate and glass for the smaller plate. The dimensions of the plates will vary widely, depending upon the type and purpose of separation to be performed, as well as the size and number of samples. The longitudinal dimension may range from as high as 100 cm or greater (for use in nucleic acid sequencing) to as low as a few centimeters. Furthermore, the system is applicable to any gel which can be prepared in a mold from a liquid gel solution.

As stated above, gels may be precast in enclosures in accordance with the present invention, generally with the removable strip still intact, for purposes of sales and storage. To avoid loss of moisture in the gel, the precast gels may be retained in sealed pouches with sufficient liquid added to maintain an appropriate moisture level.

The foregoing is offered primarily for purposes of illustration. It will be readily apparent to those skilled in the art that numerous modifications, variations and substitutions in the materials and procedures described herein may be made without departing from the spirit and scope of the invention.

What is claimed is:

1. An electrophoresis gel enclosure for use in both gel casting and electrophoresis, comprising:
   a first plate rectangular in shape:
   a second plate rectangular in shape, having shoulders along first and second opposing sides thereof and raised edges along said shoulders and a third side thereof, respectively, said raised edges arranged to receive said first plate therebetween with said first plate resting against said shoulders, said first and second plates thereby combinable to define a rectangular slab-shaped chamber of thickness defined by said shoulders; and
   a fluid-impermeable sealing sheet sized to cover said first and second plates when so combined, adhering to said raised edges and said first plate, thereby sealing said rectangular slab-shaped chamber against leakage between said first plate and said raised edges, one edge of said fluid-impermeable sealing sheet along said third side of said second plate being removable.

2. An electrophoresis gel enclosure in accordance with claim 1 in which said raised edge along said third side of said second plate includes a depression facing inward along a central portion thereof, thereby defining a gap between said raised edge and said first plate when said first and second plates are so combined.

3. An electrophoresis gel enclosure in accordance with claim 1 in which said raised edges are coplanar.

4. An electrophoresis gel enclosure in accordance with claim 1 in which said raised edges are coplanar and the height of said raised edges above said shoulders is equal to the thickness of said first plate.

5. An electrophoresis gel enclosure in accordance with claim 1 in which said shoulders are of equal height above said second plate, and each said should is of constant height along its length.

6. An electrophoresis gel enclosure in accordance with claim 1 in which said raised edges along said shoulders are defined as lateral raised edges, said lateral raised edges terminate short of the fourth side of said second plate, and said first plate is equal in length to said lateral raised edges such that when said first and second plates are so combined, said first plate and said lateral raised edges are coterminous.

7. An electrophoresis gel enclosure in accordance with claim 1 in which said fluid-impermeable sealing sheet is a polymer-based sheet coated on one side with an adhesive material, said polymer-based sheet capable of being cut by a blade.

8. A precast electrophoresis slab gel contained in a gel enclosure comprising:
   a first plate rectangular in shape;
   a second plate rectangular in shape, having shoulders along first and second opposing sides thereof and raised edges along said shoulders and a third side thereof, respectively, said raised edges arranged to receive said first plate therebetween with said first plate resting against said shoulders, said first and second plates thereby defining a rectangular slab-shaped chamber of thickness defined by said shoulders; and
   a fluid-impermeable sealing sheet covering said first and second plates, adhering to said raised edges and said first plate, thereby sealing said rectangular slab-shaped chamber against leakage between said first plate and said raised edges, one edge of said fluid-impermeable sealing sheet along said third side of said second plate being removable,
   said gel occupying said rectangular slab-shaped chamber.

9. A precast electrophoresis slab gel in accordance with claim 8 in which said raised edge along said third side of said second plate includes a depression facing inward along a central portion thereof, thereby defining a gap between said raised edge and said first plate, said gel filling said gap.

10. A precast electrophoresis slab gel in accordance with claim 8 in which said raised edges along said shoulders are defined as lateral raised edges, said lateral raised edges terminate short of the fourth side of said second plate, and said first plate is equal in length to said lateral raised edges such that said first plate and said lateral raised edges are coterminous.

11. A method for forming a slab gel and performing electrophoresis therein, said method comprising:
   (a) placing a gel-forming liquid in an enclosure comprising:
      a first plate rectangular in shape;
      a second plate rectangular in shape having shoulders along first and second opposing sides thereof and raised edges along said shoulders and a third side thereof, respectively, said raised edges arranged to receive said first plate therebetween with said first plate resting against said shoulders, said first and second plates thereby defining a rectangular slab-shaped chamber of thickness defined by said shoulders, said chamber open along the fourth side of said second plate; and
      a fluid-impermeable sealing sheet covering said first and second plates, adhering to said raised edges and said first plate, thereby holding said first plate against said shoulders and sealing said rectangular slab-shaped volume against leakage along said raised edges;
   (b) forming said gel-forming liquid thus placed in said enclosure into a gel having a first exposed edge along said fourth side;
   (c) removing a portion of said fluid-impermeable sealing sheet from said enclosure along said third side of said second plate to form a second exposed edge of said gel:
   (d) loading a sample onto said gel along said first exposed edge and impressing an electrical potential between said first and second exposed edges to cause electrophoretic separation of said sample.

12. A method in accordance with claim 11 in which step (c) comprises severing said portion of said fluid-impermeable sealing sheet from the remainder thereof with a blade, and peeling off said severed portion.

13. A method in accordance with claim 11 in which said raised edge along said third side of said second plate includes a depression facing inward along a central portion thereof, thereby defining a gap between said raised edge and said first plate, and step (a) includes filling said gap with gel-forming liquid.

14. A method in accordance with claim 11 in which said raised edges are coplanar.

15. A method in accordance with claim 11 in which said raised edges are coplanar and the height of said raised edges above said shoulders is equal to the thickness of said first plate.

* * * * *